United States Patent
White (10) Patent No.: US 8,882,499 B2
(45) Date of Patent: Nov. 11, 2014

(54) ORTHODONTIC APPLIANCE

(76) Inventor: Velton C. White, Burlington, WI (US)

(*) Notice: Subject to any disclaimer, the term of this patent is extended or adjusted under 35 U.S.C. 154(b) by 1033 days.

(21) Appl. No.: 11/755,569

(22) Filed: May 30, 2007

(65) Prior Publication Data

US 2008/0299508 A1  Dec. 4, 2008

(51) Int. Cl.
*A61C 3/00* (2006.01)
*A61C 7/00* (2006.01)

(52) U.S. Cl.
CPC .................................. *A61C 7/00* (2013.01)
USPC ............................................................ 433/18

(58) Field of Classification Search
CPC ................................... A61C 7/00; A61C 7/08
USPC ............ 433/7, 18, 20, 21, 24, 136, 138, 140, 433/214; 601/136–142
See application file for complete search history.

(56) References Cited

U.S. PATENT DOCUMENTS

| | | | |
|---|---|---|---|
| 3,975,825 A * | 8/1976 | Smith | 433/7 |
| 4,384,851 A | 5/1983 | McAndrews | |
| 4,637,796 A | 1/1987 | Korn | |
| 4,741,696 A | 5/1988 | Cetlin | |
| 4,802,849 A | 2/1989 | Collins, Jr. | |
| 4,886,451 A | 12/1989 | Cetlin | |
| 5,310,340 A | 5/1994 | Zedda | |
| 5,871,350 A | 2/1999 | Clark et al. | |
| 6,491,519 B1 | 12/2002 | Clark et al. | |
| 2005/0048433 A1 * | 3/2005 | Hilliard | 433/24 |
| 2005/0244768 A1 * | 11/2005 | Taub et al. | 433/3 |
| 2005/0260534 A1 * | 11/2005 | Belfor et al. | 433/24 |
| 2007/0065768 A1 * | 3/2007 | Nadav | 433/6 |

* cited by examiner

*Primary Examiner* — Cris L Rodriguez
*Assistant Examiner* — Matthew Nelson
(74) *Attorney, Agent, or Firm* — Dorr, Carson & Birney, P.C.

(57) ABSTRACT

An orthodontic appliance includes a flexible vesica containing a fluid, and a support structure supporting the vesica relative to the patient's dental anatomy. The support structure holds the vesica in compression against selected teeth, so that the fluid within the vesica exerts a therapeutic pressure on the teeth. For example, the support structure can include an arch-shaped trough to support a tubular vesica. The fluid can be an incompressible material, such as glycerin or water.

12 Claims, 8 Drawing Sheets

ORTHODONTIC APPLIANCE

BACKGROUND OF THE INVENTION

1. Field of the Invention

The present invention relates generally to the field of orthodontics. More specifically, the present invention discloses an orthodontic appliance using a resilient vesica filled with a fluid to position teeth.

2. Statement of the Problem

When reduced to its simplest principles, orthodontic correction involves the steps of placing spring devices adjacent to individual teeth or groups of teeth according to a predetermined treatment plan; loading those springs with potential energy; mechanically directing that stored energy to the crown of a tooth (or a group of teeth) and then over time, allowing that stored energy to dissipate as the springs elicit a physiological response from the living structures, evidenced by desirable tooth movement.

By design, orthodontic springs generate force levels that are regulated or throttled to fall within a range known to be safe and effective for initiating the physiological response of tooth movement. In response to gentle and continuous forces, the underlying bone supporting the roots of a tooth undergo a process involving the removal of bone (resorbtion) in the direction of movement of the root, along with the creation of new bone (osteogenesis) in the wake of root/tooth movement. This generally accepted model of tooth movement provides the basis for orthodontists to effectively reposition teeth according to a treatment plan.

In user the springs referenced above can take on a wide range of forms and configurations. Such springs can be formed from many materials ranging from latex and polymeric elastomeric materials, vacu-formed shells of olefin plastics and polycarbonate, to austenitic stainless steel, and other metallic alloys containing titanium, and cobalt as examples. Mechanical force generation can also be created by jack screws and other positive thread or magnetically-driven micro-mechanical devices. In those cases, the stored energy referenced above can be imparted directly to the skeletal structure of the face and skull, and in a sense, those boney structures themselves become the resistive spring. In those cases, the growth potential of young and rapidly growing adolescent patients can be desirably redirected to compensate for facial imbalances and anatomical deficiencies. For adults, application of gentle and continuous forces directly to bone can elicit other types of corrective boney responses. All of the efforts at correcting and reshaping malleable bone are generally referred to as bone remodeling.

As described above, the physiological responses allowing movement of a tooth's root through its boney support will occur only after forces failing within a range of biologically effective values are directed to the tooth. The osteo-based process of tooth movement involves complex cellular-level biological phenomena but those ideal forces, as well as forces above and below biologically ideal values can be categorized as subliminal, optimal or excessive, as follows.

Subliminal: When forces are below a minimum level, a tooth may exhibit slight repositioning as allowed by the tensing the periodontal fibers, but other than that, no true enduring, physiologically-based bodily movement of the tooth will be initiated. Such light forces are very unlikely to pose any concern of injury or trauma.

Optimal: When forces directed to the roots of the teeth fall within an ideal range, the osteogenetic processes proceed at a natural rate, without pathology or trauma to the surrounding living tissues/structures. The bioengineering of orthodontic armamentarium strives to deliver forces of this magnitude to effect correction. It is thought that the introduction of orthodontic forces triggers an otherwise natural balancing response of the living system and as such, forces within this range are unlikely to pose any concern of injury or trauma.

Excessive: Forces impinging on the tooth's root that exceed a maximum physiological force can cause injury to the surrounding tissues and the tooth itself. In such cases, any previously established rate of tooth movement will be markedly slowed and then it will stop. Excessive forces can result in patient pain stemming from such insult. Necrotic conditions within the periodontal socket, the periodontal membrane and the surrounding bone may result. In particular, the apical tip of the tooth's root may be blunted or resorbed, resulting in long axis shortening, a decrease in anchorage and other destructive long-term sequelae.

To quantify forces required for tooth movement, orthodontists have traditionally used an approach beginning with the determination of the area of the root of a tooth in plan-form as viewed perpendicular to the axis of movement. In other words, even though curved or cone shaped, and even though some teeth have multiple roots, a two-dimensional plan-form profile of the root structure is assessed and an estimate is made to arrive at a value for the area of root ensconced in bone. Next, a force constant will be established per unit area. For example, the multiple roots of a statistically average-sized lower first molar as viewed from the mesial may have a combined root plan-form profile of about 72 $mm^2$. Using a value of 5 grams per $mm^2$ as a physiological force constant, it can then be said that a distally-directed force of 360 grams (5×72) would constitute an ideal physiological force for moving a lower first molar of average size in the distal direction.

In practice, a rule of thumb value such as "360 grams to distalize a lower molar" will be established but an orthodontist may moderate that value somewhat lower for smaller than average-sized teeth or use a somewhat higher value than 360 grams for larger teeth. Further, the rule of thumb value may be further adjusted to accommodate patient age, sex and other holistic health factors. There is no practical need to precisely calculate exact root area or to precisely define target forces due to the fact that the living structure is tolerant of a relatively wide range of forces.

The example above involved the distal movement of a lower first molar. The same force constant value used for distal movement may be used for either distal or mesial movement and further, the force constant can be reliably used for all of the teeth being moved mesially or distally. Other force constants apply when considering the repositioning of roots in a lingual or labial/buccal direction. Similarly, still other force constants apply to the intrusion or extrusion of teeth. All of these considerations involve the initial step of estimating a realistic value for the plan-form area of the root as viewed along the axis of intended movement. Then the area resultant is multiplied by the appropriate force constant related to the intended direction of movement. In all cases, the objective is to determine the optimal force levels, on a tooth by tooth basis, to most efficiently move a tooth according to a treatment plan.

Even though the foregoing discussion covering methods for determining orthodontic force levels may generally represent traditional thinking in the field, many shortcomings and compromises are typically involved in the everyday delivery of orthodontic forces to teeth during orthodontic treatment. For example, during the early stages of treatment, the teeth and the arch slots of the brackets attached to them are chaotically positioned around both dental arches. As such, it will be determined that some of the teeth are positioned far from their desired finished positions and orientations while other teeth may be nearly in a correct or ideal position as is. Nonetheless, one continuous, monolithic archwire is normally installed in the bracket arch slots to begin the process of establishing order to all of the teeth. Such an archwire falls in the general class of orthodontic springs discussed earlier, where energy is stored as the spring is deflected. In an archwire's efforts to follow the lowest energy trajectory as it passes through each of the series of mal-positioned arch slots, varying degrees of archwire deflection and torsional twisting will be induced. Certain segments of the wire may exhibit high deflection, which can be associated with high levels of stored energy and conversely, segments of low archwire deflection store less energy. Teeth attached to the archwire within zones of high deflection will inherently receive significantly higher force levels and other teeth positioned within zones of low deflection will inherently receive much lower levels of corrective force. The thrust of this discussion is to convey the point that traditionally the levels of force delivered to any one tooth by an archwire is exponentially proportional to the extent to which the tooth is mal-positioned. Those archwire-generated forces are in no way proportional or in no way related to the area of the root supported by the underlying bone of the individual teeth that the archwire is attached to. It can be said that the archwire treats all brackets the same, regardless of the size of the tooth the bracket is attached to. Because of this, it is possible for small teeth to receive injuriously high corrective forces and for large teeth to receive ineffective, low forces from the archwire. In these instances, neither the large nor the small tooth will respond nearly as rapidly as when ideal forces are applied and in fact, those teeth may not move appreciably at all, and worse, the high force values associated with high archwire deflection may cause injury to the surrounding tissues as described earlier.

In practice, some skilled orthodontists use a number of methods to regulate the forces that are delivered to individual teeth. Additional wire length incorporated into the archwire, in the form of various types of loops and helices are sometimes installed to reduce the effective spring rate of the archwire. Accommodative bends intended to reduce the degree of deflection represent another means orthodontists use to differentiate forces, but such methods are by in large an art, directly dependant on the skill and craftsmanship of the individual doctor. Such steps can be called an art due to the fact that in practice, the net effect of such archwire modifications is seldom if ever quantified from a bioengineering standpoint and at most, represent a best guess on the part of the practitioner. Installation of such force-regulating features into the oral hardware, and the associated need for continual adjustment and activation of those features is time consuming and adds to the cost of treatment. Further, such force-regulating features invite breakage, can cause patient discomfort and can contribute to compromised hygiene. As a final comment on the use of force-regulating archwire features, current trends in orthodontics point away from the use of such features. Force regulation is more commonly relegated to optimizing the mechanical properties of the monolithic archwires themselves. Super-elastic (austenitic) nickel-titanium archwires exhibit a nearly flat stress/strain relationship and may represent an improvement over methods of the past, but use of such archwires has other reciprocal drawbacks, namely a very limited modulus of stiffness. They are very weak and can be effectively used only during certain phases of treatment.

To summarize the shortcomings of current methods, many of the springs used in orthodontic treatment exhibit an overly rapid spring rate. This is often due to space constraints in the mouth where space does not allow larger springs configured for a more desirable lower spring rate as described above. It is also due to the fact that lighter wire with a desirably lower spring rate tends to be more delicate and as such they are susceptible to distortion and breakage in the mouths of active and uncooperative adolescent patients.

Other problems triggered by the situation where an archwire exerts exponentially stiffer forces depending on the degree of mal-positioning exhibited by any one tooth can occur in a number of situations. Stiff, rapid rate springs that exhibit an exponentially increasing spring rate, such as those currently used in orthodontics may have a tendency to at first exert injuriously high forces before rapidly declining through the ideal force range and then dropping off to below a threshold force level, all within a matter of weeks or even days. This range from "too high to too low" progresses as a tooth responds to the forces and moves, and thereby unloads the driving spring. Orthodontic springs formed from latex or elastomeric polymers similarly tend to start out delivering high forces but then relax over the course of a day or two due to molecular slippage (creep) and water absorption. A gentle, constant and steady biological force is known to be ideal for tooth movement, but as can be appreciated from the foregoing, current practice of orthodontics involves forces that are often unknown and out of control. The unfortunate result is that a saw-tooth profile of forces are typically delivered to each tooth, where reactivation initiates a new cycle of high but then rapidly degrading forces. Such high, then low intermittent forces have been called "insult and repair" and as such are generally agreed by orthodontists as being undesirable and to be avoided to the extent possible. One reason intermittent forces are to be avoided is that the physiological processes of tooth movement, once initiated are best kept going. If allowed to stop, they are more difficult to get started again.

Solution to the Problem. The present invention addresses several of the shortcomings of the prior art in this field by providing an orthodontic aligner that employs a fluid-filled vesica to apply relatively uniform hydraulic pressure on the teeth within the optimal range of force, as described above. This approach helps to eliminate the problems associated with excessive forces or subliminal forces that have sometimes occurred with conventional orthodontic appliances.

SUMMARY OF THE INVENTION

This invention provides an orthodontic appliance having a flexible vesica containing a fluid, and a support structure supporting the vesica relative to the patient's dental anatomy. The support structure holds the vesica in compression against selected teeth, so that the fluid within the vesica exerts a therapeutic pressure on the teeth. For example, the support structure can include an arch-shaped trough to support a tubular vesica. The fluid can be an incompressible material, such as glycerin or water.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
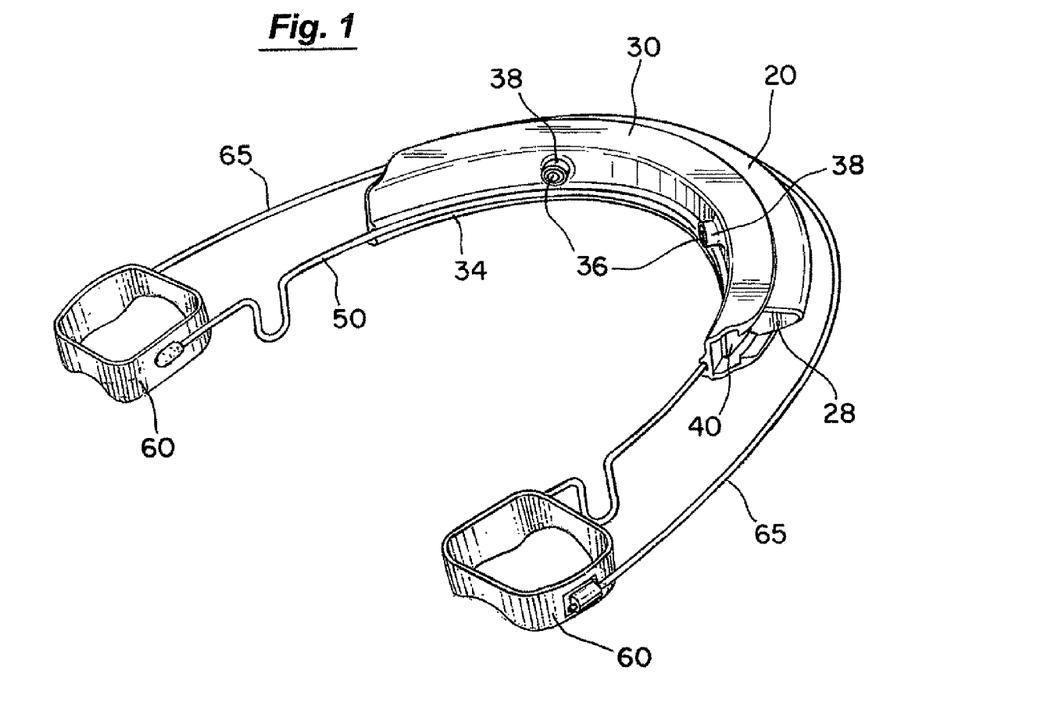
FIG. 1 is a perspective view of an orthodontic appliance embodying the present invention.
Figure 11:
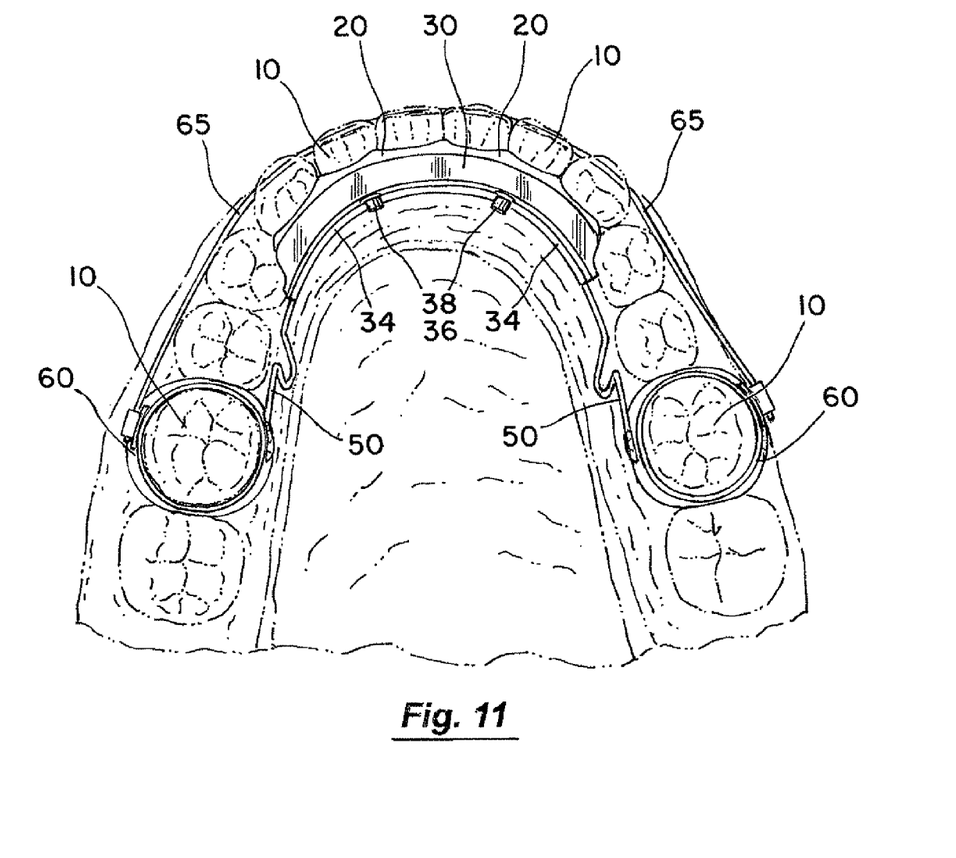
FIG. 11 is a perspective view of the orthodontic appliance of FIG. 1 installed on a patient's mandibular teeth 10.
Figure 13:
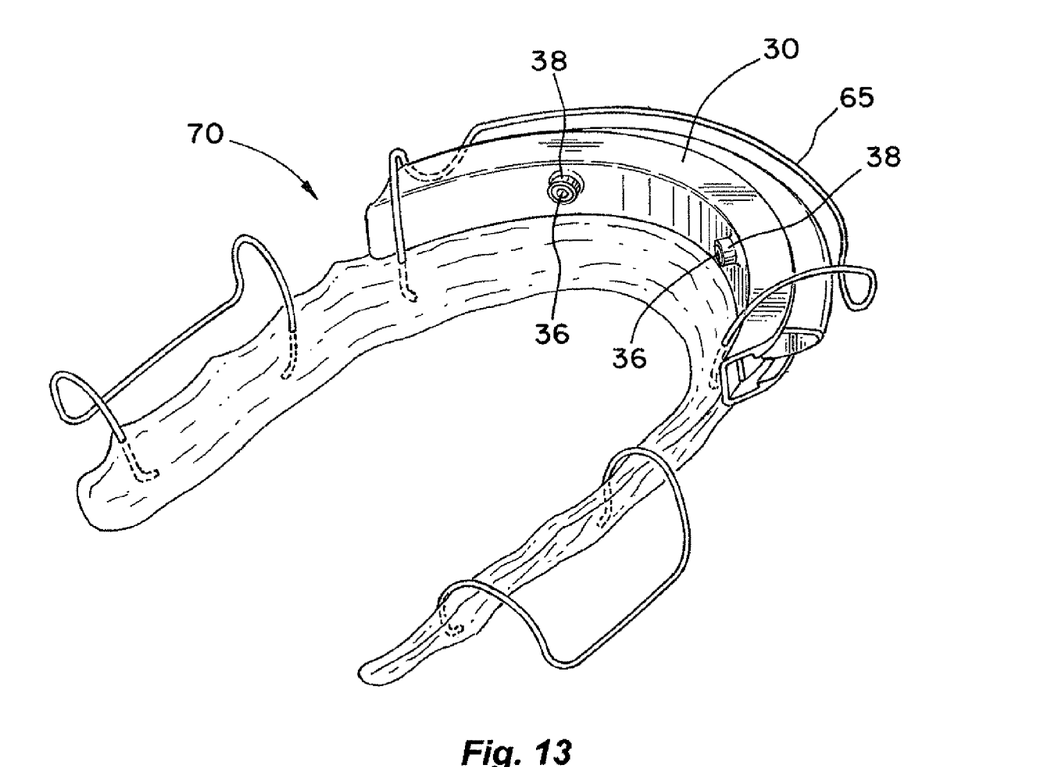
FIG. 13 is a perspective view of a removable orthodontic appliance 70 embodying the present invention.
Figure 14:
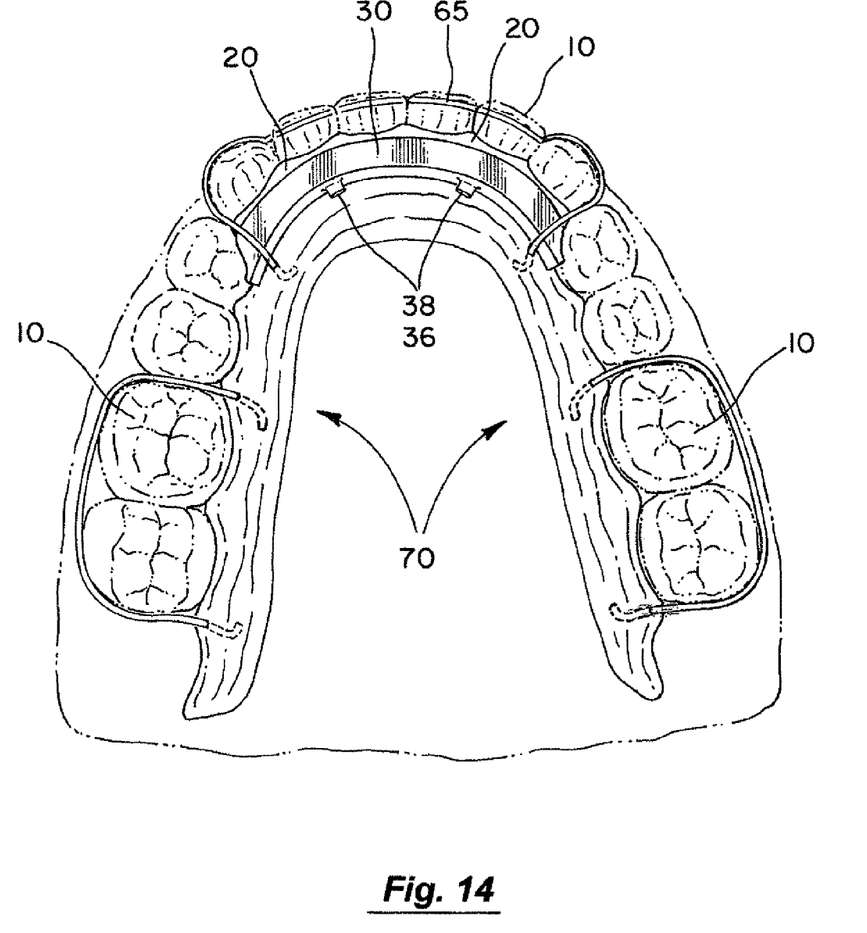
FIG. 14 is a top view of the removable orthodontic appliance 70 in FIG. 13 installed on a patient's mandibular teeth.

FIG. 1 is a perspective view of an embodiment of the present invention in a fixed orthodontic appliance. The major components in this embodiment include a vesica 20 containing a fluid, and a support structure such as an arch-shaped trough 30 for holding the vesica 20 relative to the patient's dental anatomy. The support structure holds the vesica 20 in compression against selected teeth so that the fluid 24 within the vesica 20 exerts a therapeutic pressure on the teeth. The orthodontic appliance can configured as a fixed appliance anchored to bands or crowns 60 attached to the molars, as illustrated in FIGS. 1 and 11. Alternatively, the appliance be configured as a removable appliance 70, as shown in FIGS. 13 and 14.

Figure 2:
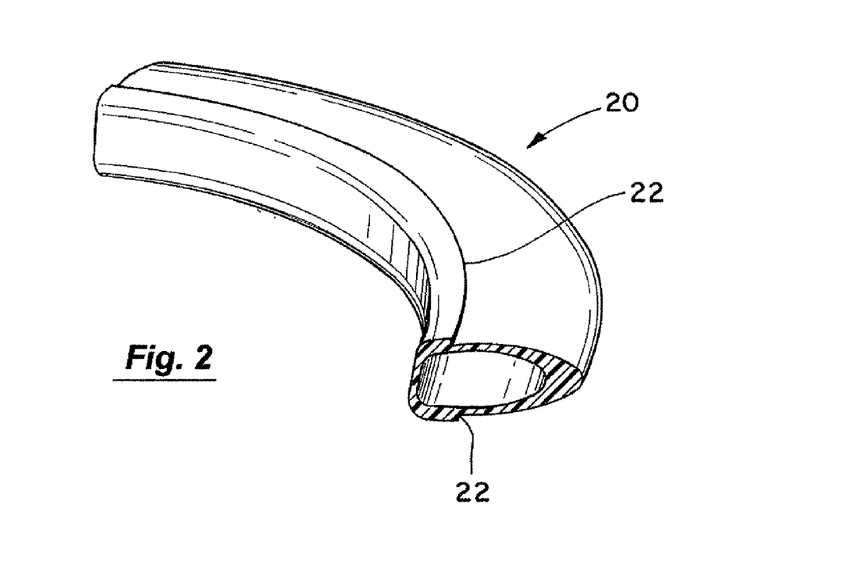
FIG. 2 is a perspective view of a section of the vesica 20.

FIG. 2 is a perspective view of a section of the vesica 20 shown in FIG. 1. In this embodiment, the vesica 20 has a hollow, soft, rubber-like tubular extruded profile. Even though during manufacture the extruded tubular profile of the vesica 20 may be formed lineally, in use a curved segment of the material is typically used as is allowed by its soft and elastic qualities. Its resilient mechanical properties allow the extruded profile to easily conform as required in compliance with the dental arch form. Possible methods and materials for forming the extruded profile of the vesica 20 include latex lamination and extrusion of medical-grade silicone rubber.

Figure 3:
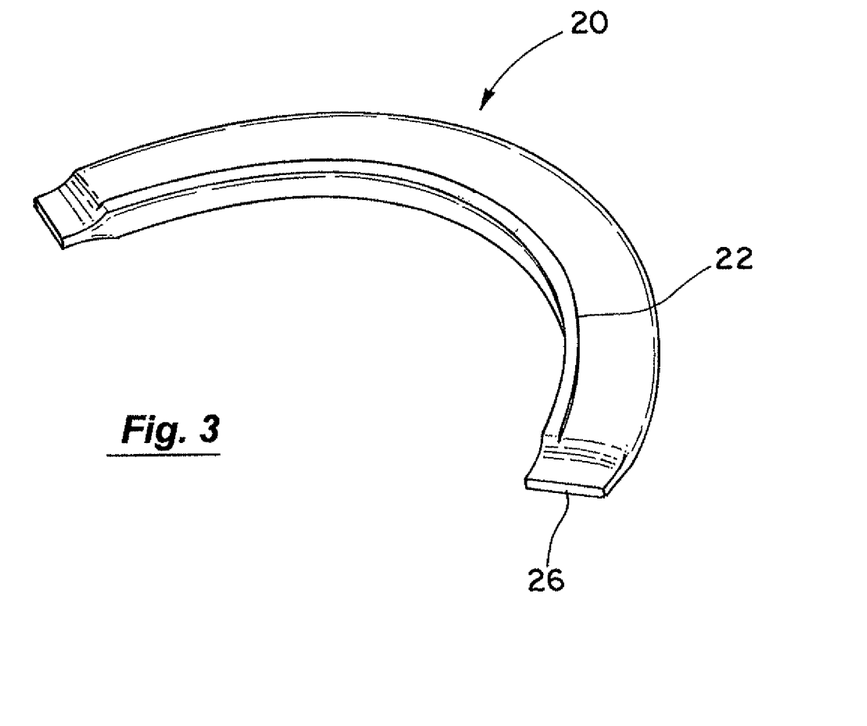
FIG. 3 is a perspective view of an embodiment of the vesica 20 with sealed ends 26.
Figure 4:
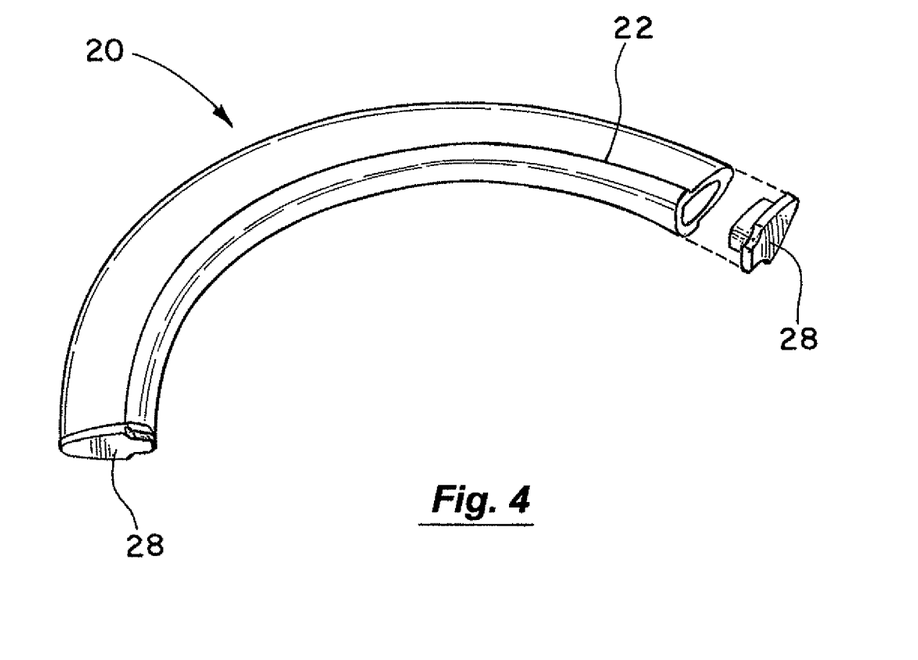
FIG. 4 is a perspective view of an embodiment o the vesica 20 with end caps 28.

The ends of a segment of the extruded profile can be closed or sealed to form an enclosed volume filled with a fluid 24 within the vesica 20. For example, FIG. 3 illustrates a vesica 20 with sealed ends 26. Means for sealing include ultrasonic welding, heat sealing, chemical bonding and the like. Alternatively, separate end plugs 28 as shown in FIG. 4 can be used to seal the ends of the extruded profile to contain a fluid. End plugs 28 can be retained in the ends of the vesica 20 mechanically by barb fitting, chemical bonding, ultrasonic welding and the like, as well as combinations of these means. End plugs 28 can be formed from soft, non-toxic polymers or composite materials, but should typically be harder than the material of the vesica 20. FIG. 4 displays a vesica 20 according to the present invention complete with end plugs 28 and curved to comply with the lingual archform of an orthodontic patient. Preferably, a liquid or other relatively incompressible fluid is contained within the vesica 20, but air or other inert gas could be used as the fluid. Vegetable glycerin, water and mineral oil are examples of suitable fluids, with vegetable glycerin being preferable. A non-toxic liquid should be used due to the remote possibility of the vesica 20 being punctured and failing in the mouth.

Preferably, the vesica 20 is an elongated tubular member with flexible walls and closed ends suitable for containing a fluid, as depicted in the accompanying drawings. This embodiment requires a minimal amount of space within the patient's mouth. It should also be understood that the vesica could have any desired cross-sectional shape. However, the vesica could any type of bladder or enclosed volume having a shape suitable for exerting hydraulic pressure on a selected set of a patient's teeth.

With the vesica 20 positioned in the mouth lingually by its support structure, the vesica 20 becomes slightly pressurized when the elastomeric structure of the vesica 20 is urged against the teeth. This deformation of the vesica 20 against the teeth tends to compress the fluid 24 within the vesica 20, and places the elastomeric structure of the vesica 20 uniformly in slight tension. This is the result of the fluid 24 within the vesica 20 hydraulically-distributing pressure equally throughout the contained volume of a vesica 20. As the pressure is hydraulically distributed throughout the vesica's structure, the vesica 20 becomes evenly tensed at all points and exerts a substantially uniform pressure over its entire exterior surface. This pressure is applied to any teeth in contact with the vesica 20. The pressure remains relatively constant for the surface area of all teeth in contact with the vesica 20. This uniformity in pressure helps to prevent both excessive forces and subliminal forces that have sometimes occurred with conventional orthodontic appliances.

Figure 5:
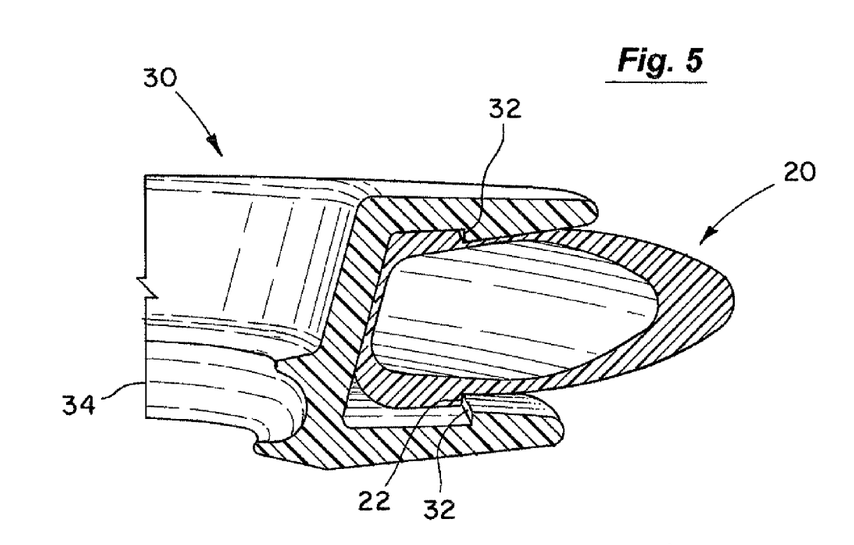
FIG. 5 is a cross-sectional view of the assembled vesica 20 and trough 30.
Figure 6:
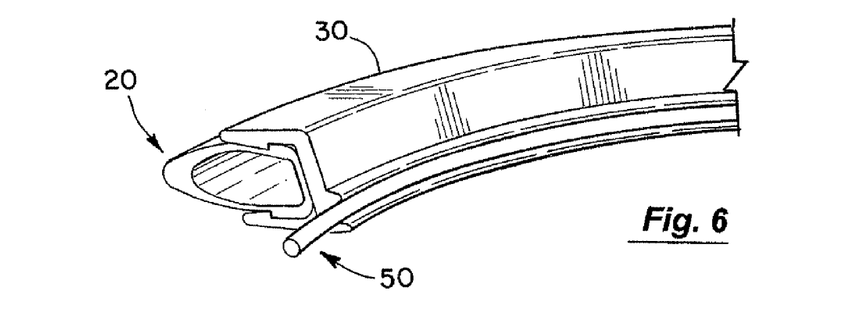
FIG. 6 is a cross-sectional view of the assembled vesica 20, trough 30 and archwire 50.

For example, in the embodiment shown in FIG. 5, the vesica 20 is retained and support by an arch-shaped trough 30. The inter-fitting relationship between the barbed edges 32 on the upper and lower arms of the trough 30 and the corresponding grooves or slots 22 on the top and bottom of the vesica 20 serve to retain the lingual portion of the vesica 20 within the trough 30. However, the labial portion of the vesica 20 extends outward beyond the arms of the trough 30 so that it can contact a patient's teeth. The vesica 20 is installed in the trough 30 by working it into place, either from the end and sliding it into position or using finger pressure to snap it into position from the forward opening of the trough 30. A tool or a fixture may be used for this purpose. The reader should appreciate that as described earlier the vesica 20 during use is slightly pressurized and its structure, being elastomeric allows a slight enlargement or outward bulging of the vesica 20 at all points. The slight outward pressure-induced expansion of the vesica 20 further serves to more positively hold the vesica 20 in a retentive relationship within the trough 30.

The trough 30 itself can be formed from various materials including polymers or heat-formable dental materials. Alternatively, the trough 30 may be injection molded to a statistically-average size or range of sizes, such molding preferably to be based on a heat-formable material. Heat-formability permits the trough portion of the appliance to be adapted or shaped as required relative to a patient's anatomy on a caseby-case basis. The materials suitable for forming a trough can exhibit slight ductility at room temperature but generally, the trough 30 should exhibit sufficient mechanical integrity to remain in an essentially rigid configuration once formed and allowed to cool, to effectively hold the vesica 20. The present invention anticipates a trough profile that has sufficient rounding and contouring of all of its outer edges and corners so that the trough 30, once integrated into a finished appliance can serve in the mouth without causing discomfort to the tongue, cheeks, lips and gums.

A useful attribute of the material used for forming a trough 30 is that it be chemically bondable to standard methyl methacrylate powder/liquid-monomer-type dental acrylic as is used extensively in dentistry and orthodontics. Methyl methacrylate is used for forming retainers and other mouth or tooth-compliant appliances. If the trough 30 is formed from a material chemically retentive to methyl methacrylate powder/liquid-monomer-type dental acrylic, it is capable of being integrated integrally with dental acrylic forming the body of an orthodontic appliance. By casting the trough 30 within a mass of dental acrylic, a dental laboratory technician can fabricate an orthodontic appliance that complies with the anatomy of a patient's palate, the margins of the teeth, the soft tissues and so on. In such cases, metallic ball clasps or Adams-type clasps can also be embedded in the dental acrylic for retention of the appliance in the mouth. As such, the completed appliance would be considered a removable-type appliance. In other words, a patient may remove the appliance at any time such as for social functions and eating. An example of a removable appliance 70 embodying the present invention is illustrated in FIG. 13. FIG. 14 is a corresponding top view of the removable appliance 70 installed on a patient's mandibular teeth.

Another possible embodiment of the present invention mounts a fluid-filled vesica within the cavity of a thin plastic aligner to exert a therapeutic pressure on selected teeth. For example, the vesica can be attached to the interior surface of the lingual wall of the aligner cavity to exert labially-directed pressure. The labial wall of the aligner can be shifted labially or equipped with windows or cutouts to accommodate labial movement of selected teeth in response to the pressure exerted by the vesica.

Returning to considerations of the attributes of a trough 30 not configured for being integrated into a larger methyl methacrylate acrylic-type appliance, one can appreciate that other means for positioning and retaining the appliance in the mouth are needed. Specifically, without the larger acrylic mass, the appliance has no engagement to impart stability from the palate and soft tissues. Further, such an appliance can be devoid of acrylic structure in which to mount retentive clasps. Because of these limitations, such an embodiment may require a heavy arch-conforming wire 50 to be affixed to the trough 30 allowing for fixed attachment within the mouth. A receptive feature (e.g., a track or clip 34) for aligning and attaching such a wire 34 is anticipated within the profile of the trough 30 in FIGS. 5, 6, 8 and 9.

Returning to the embodiment depicted in FIG. 1, a heavy wire 50, such as a wire with at least diameter of 0.045 in. or larger of partially work-hardened 304 stainless steel extends distally from each side of the trough 30 to the first molar region. There it attaches rigidly by brazing or welding to steel bands or crowns 60 seated on the first molars as shown in FIGS. 5 and 11. As above, if the attachment is permanent (i.e. fixedly brazed or welded), the appliance is considered to be a fixed-type appliance. The attachment means between the heavy wire 50 and the molar band or crown 60 may alternatively use a fixed removable-type means of attachment. Fixed removable attachments require that horizontal tubes, horizontal sheaths or single or twin vertical tubes be attached to the cemented molar-borne bands or crowns 60. The distal ends of the heavy wire 50 receive rigidly mounted steel devices that positively plug into such receiving features mounted on the molars. Fixed removable attachments enable an orthodontist or an orthodontic staff member to remove the appliance as may be needed during a patient's office appointment, but otherwise, the patient cannot remove the appliance between appointments.

The degree of pressure exerted by the vesica 20 can be readily adjusted over the course of treatment, if desired, by adjustment of the position of the vesica 20 relative to the support structure and teeth. Removable and fixed removable configurations are seen as the most appropriate configurations for the present invention due to the fact that one or more activations of the appliance may be required during treatment to adjust the position of the vesica 20 and the pressure that it exerts on the teeth. Such activations are most conveniently accomplished at chair-side with the appliance removed from the mouth, but the current invention can accommodate inter-oral activation and thus a fixed configuration can serve in treatment. As will become apparent, one or more activations may be required during the course of treatment. Such activations are to compensate for reduced pressurization of the vesica resulting from the teeth desirably responding to forces from the vesica and repositioning.

Referring again to the trough 30 and its application, the configuration of the raw material used to form the trough 30 may be produced by an extrusion process in continuous straight lengths. In the case of straight lengths, they will be trimmed to a length required for an individual appliance in the process of custom-adapting an appliance for an individual patient's treatment. A trimmed but straight length of the trough material may be adapted to the accurate shape required for an appliance by first heating it and forming it generally in an approximation of the U-shape of the anterior portion of the dental arch. Once generally formed, it may then be re-heated permitting additional and more accurate forming so that its quasi-circular arc shape is approximately concentric with the arc defined by the anterior lingual segment of the teeth, but offset from that arc by a predetermined distance or predetermined gap. Stated in different terms, the trough 30, once appropriately shaped and held in concentric relation adjacent to a patient's working model should demonstrate a gap between itself and the approximated shape of the arc formed by the anterior teeth. The approximated arc formed by the anterior teeth must be visualized, in anticipation of the ideal arch form that will result from treatment. Such a gap between the approximated, tooth-defined arc and the trough 30 can be described as a gap of a pre-determined dimension. The actual dimensional value of that gap is determined by assessment of the dimensions of the vesica 20, considering that it is located intermediate between the trough 30 and the teeth 10, while anticipating an average degree of compression that the vesica 20 will encounter as it is positioned into contact, first with the most errant teeth, and the degree of compression the vesica 20 will require to be effective in moving all of the teeth into an ideal anterior arch form. Another factor a laboratory technician should consider in adapting such an appliance involves the fact that a steel bow 65 will typically be present on the labial side of the teeth opposite to the vesica 20. Such a bow 65 is known as a Hawley bow, and is commonly provided with laboratory-produced appliances. A Hawley bow serves as a stop for labial movement of teeth. Typically, labially-directed forces from the lingual need only move teeth into contact against the bow, so that the desired arch form is defined by the bow. When such a bow 65 is present, the vesica 20 is intended to gather the anterior teeth and push them to the bow, where they then stop. The bow 65 is configured to allow sufficient space and an appropriate morphological arch form shape so that with all of the teeth moved against it, those teeth are in generally good position and have sufficient space, but crowding is eliminated.

Additional force from the vesica 20 occurring after the teeth move labially and into first contact with the bow 65 can serve to slowly unwind undesirable rotations of the teeth. The present invention should be considered as optionally incorporating a rigid Hawley bow as described, particularly when considering removable versions that are cast within an acrylic mass.

Figure 7:
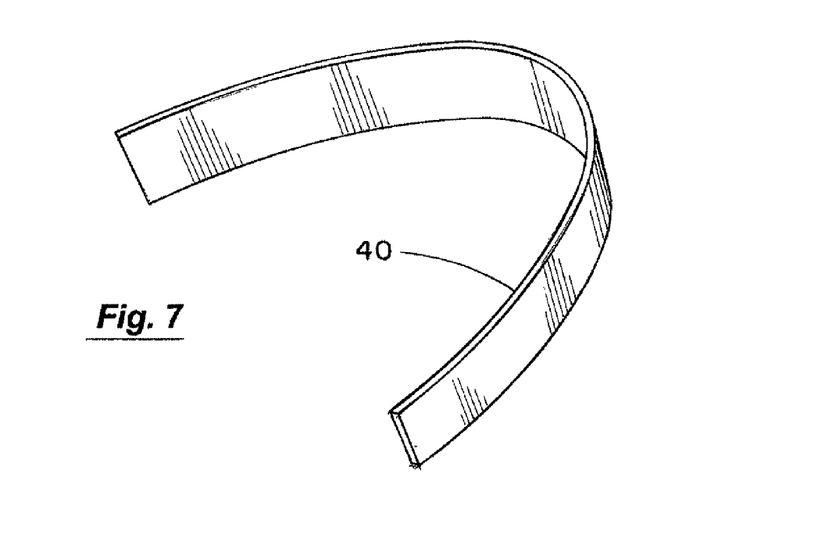
FIG. 7 is a perspective view of an activation ribbon 40.
Figure 8:
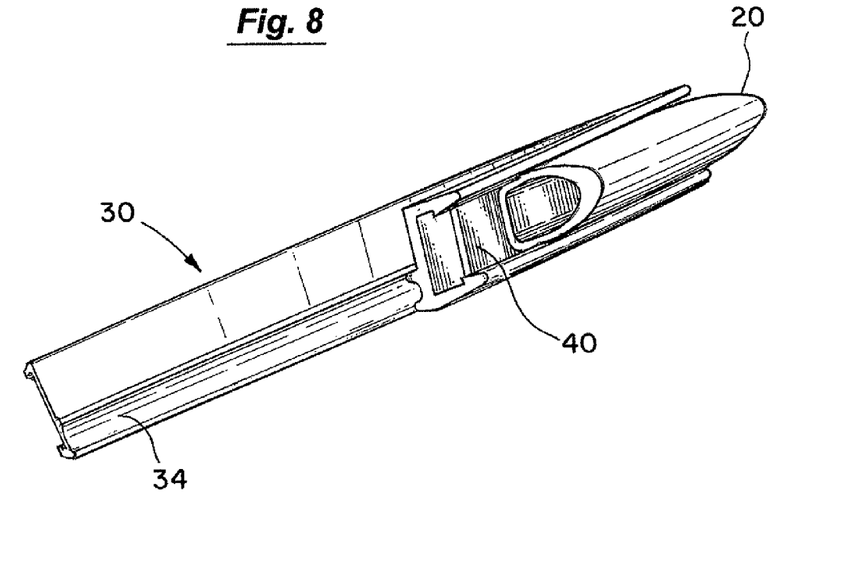
FIG. 8 is a cut-away perspective view of the assembled vesica 20, trough 30 and activation ribbon 40.
Figure 9:
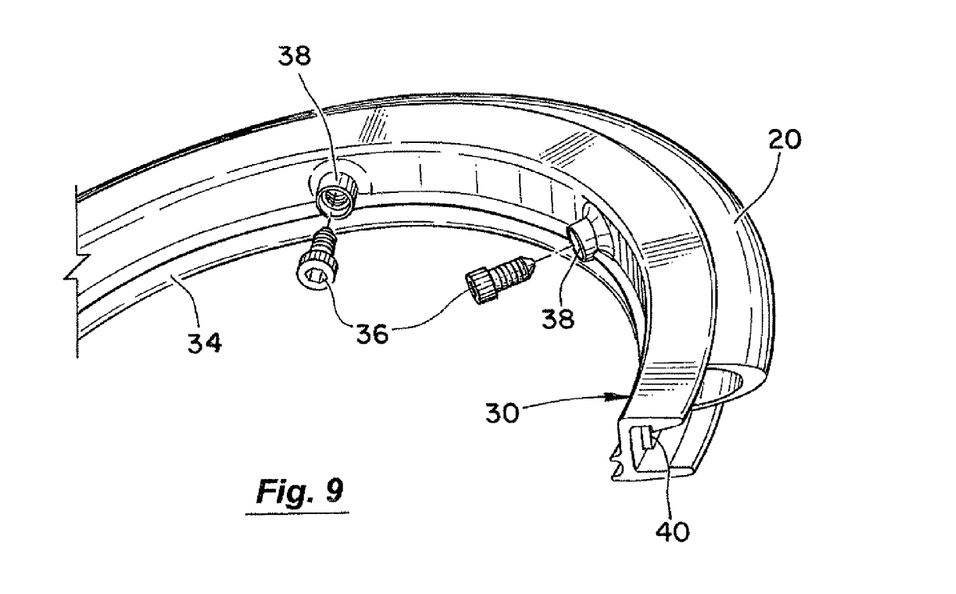
FIG. 9 is a perspective view of the assembled vesica 20, activation ribbon 40 and trough 30 with a series of adjustment screws 36.

A reduction in the light pressurization described above in response to the teeth being moved is one reason that the orthodontic appliance may require activation during treatment. For activation, an example of an activation ribbon 40 is shown in FIG. 7. The activation ribbon 40 can be positioned behind the vesica 20 (i.e., placed between the vesica 20 and the floor of the trough 30) as shown in FIGS. 8 and 9. The activation ribbon 40 may be formed from an appropriately-sized, curved, malleable metallic strip or a polymeric ribbon. Its edges and corners may be rounded allowing a technician, doctor or staff member to wedge the activation ribbon 40 between the floor of the trough 30 and the lingual wall of the vesica 20 without catching or puncturing the vesica 20. Once wedged in place, the activation ribbon 40 can be pushed further so that the ribbon 40 is centered laterally around the extent of the trough 30. The activation ribbon 40 can be installed in the appliance during treatment in this manner provided the appliance is of the removable or fixed removable configuration. Removability of the appliance allows the activation ribbon 40 to be installed as described above. If the appliance is of the fixed configuration however, the ribbon 40 must usually be installed prior to fixedly seating the appliance on the molars and other means must be employed for activation, as described below.

Essentially, the activation ribbon 40 functions to reactivate the appliance during treatment by restoring the light pressurization of the fluid 24 trapped inside the vesica 20 and simultaneously, activation physically repositions the tooth-contacting leading edge of the vesica 20 further toward the teeth 10, Both of these actions are intended to restore the beginning aggressiveness of the vesica 20 against the teeth 10. The present invention also anticipates activation ribbons 40 of progressively thicker dimensions over the course of treatment. Thicker activation ribbons 40 can be used for multiple activations as treatment progresses. For example, treatment can be started with no activation ribbons in place, then after a time, an activation ribbon with a thickness of 0.010 in., or about ¼ mm can be added. Still later in treatment a second such ribbon may be placed in the tough, or the original 0.010 in. ribbon may be removed and replaced with a 0.020 in. ribbon (½ mm).

As can be appreciated from the foregoing description of the removable, fixed removable and fixed configurations of the appliance, activation poses more of a challenge when the fixed version is used in treatment. The present invention provides features accommodative of the need for activation of all configurations but which are particularly applicable to the fixed version of the appliance. FIG. 9 illustrates an embodiment in which a number of threaded bores 38 pass through the floor of the trough 30. The internal diameter of each bore 38 is threaded to receive an activation screw 36. The activation screws 36, preferably formed from a polymer, are oriented as shown in FIG. 9. The screw-receiving structures shown in FIG. 9 have a hood portion extending lingually from the trough 30 at a distance slightly exceeding that of the labial-lingual length of the head of the activation screw 36. The hood feature anticipates cases where the appliance is embedded in dental acrylic. During the curing of dental acrylic, the polymerizing mass passes through a flowing stage before it cures structurally. The hood portion of the screw-receiving structure serves to shield the threads making it much less likely that uncured acrylic material can undesirably flow into the threads.

The screw-receiving structures may be separate auxiliary parts that bond to the trough 30, if needed. In that case, the bore of the auxiliary parts as well as the coincident bore through the trough may be tapped (threaded) together after such joining/bonding. The bore through both an auxiliary part and the trough 30 may be drilled after bonding and then tapped to insure concentricity. In any event, the activation screws 36, when tightened act against the activation ribbon 40 by passing through the auxiliary part and the trough 30 to contact the lingual side of the activation ribbon 40. Tightening the activation screws 36 acts by pushing the activation ribbon 40 further against the lingual wall of the vesica 20.

Figure 10A:
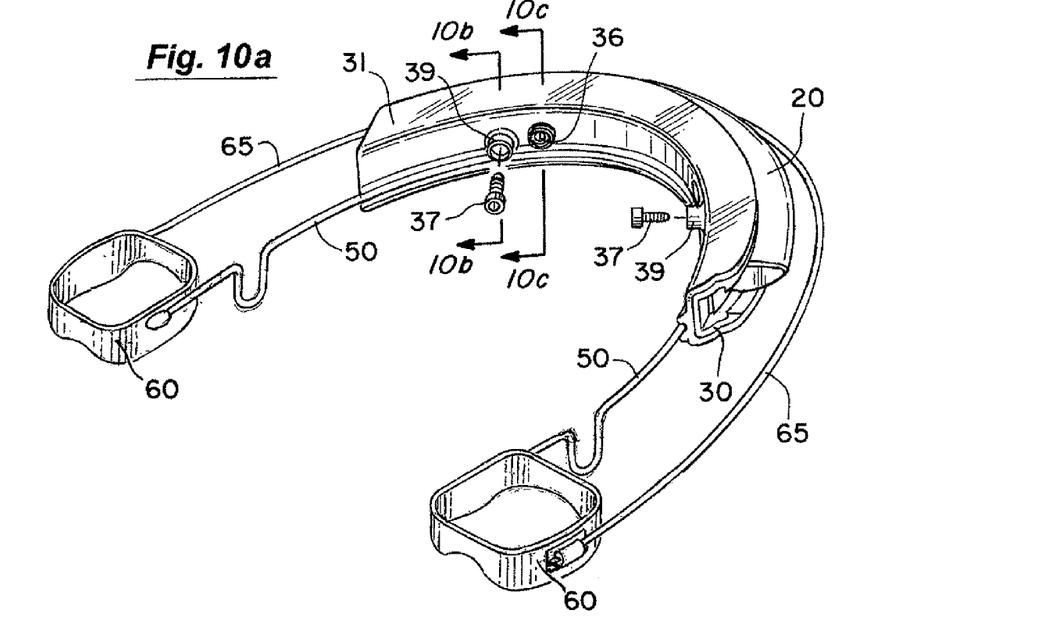
FIG. 10a is a perspective view of an embodiment of the present invention with a support bracket 31 adjustably supporting the trough 30 to provide an additional range of adjustment for the vesica 20 relative to the patient's teeth.
Figure 10B:
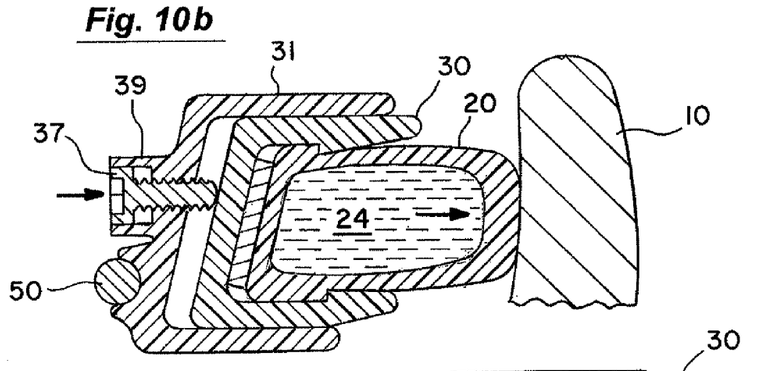
FIG. 10b is a vertical cross-sectional view corresponding to FIG. 10a illustrating adjustment of the positions of the trough 30 and vesica 20 relative to the support bracket 31 via adjustment screws 37.
Figure 10C:
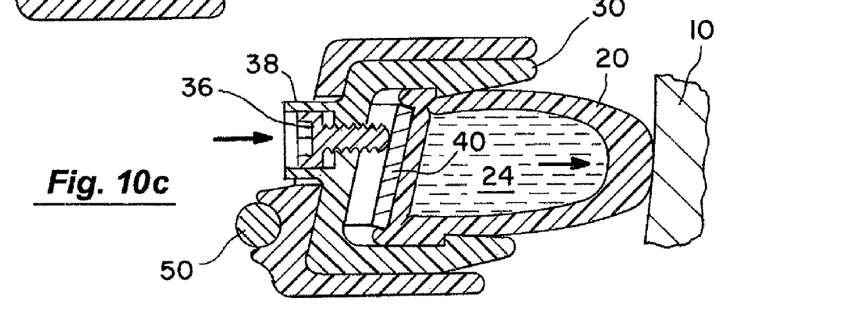
FIG. 10c is another vertical cross-sectional view corresponding to FIG. 10a illustrating adjustment of the position of the vesica 20 relative to the trough 30 and support bracket 31 via adjustment screws 36.

FIG. 10*a* is a perspective view of another embodiment expanding the concept of adjustability illustrated in FIG. 9. FIGS. 10*b* and 10*c* are corresponding cross-sectional views. This embodiment includes a support bracket 31 adjustably supporting the trough 30. In the specific embodiment shown in FIGS. 10*a*-10*c*, both the support bracket 31 and trough 30 are generally arch-shaped. The support bracket 31 has a generally U-shaped vertical cross-section with dimensions that allow the trough 30 to be inserted into the support bracket 31 in sliding engagement along an anterior-posterior axis. A number of adjustment screws 37 are threaded through holes 39 in the lingual surface of the support bracket 31 and contact the lingual surface of the trough 30 to adjust the spacing between the support bracket 31 and trough 30, as illustrated in the cross-sectional view provided in FIG. 10*b*. For example, tightening the adjustment screws 37 moves the trough 30 and vesica 20 forward, which increases the pressure exerted by the vesica 20 on the teeth. In other words, the support bracket 31 and its adjustment screws 37 provide a second, additional range of adjustment for positioning the vesica 20. This is in addition to the range of adjustment made possible by the adjustment screws 36 threaded through the trough 30 as shown in the cross-sectional view provided in FIG. 10*c*. It should also be understood that other types of adjustment mechanisms could be substituted to position the trough 30 and vesica 20.

FIG. 11 illustrates an orthodontic appliance of the fixed configuration of an orthodontic appliance on a patient's lower arch. The same configuration can be applied to the upper arch. Both the upper and lower arches can be treated with appliances of the present invention. Similarly, the appliance can be converted through the reversal of the orientation of its components so as to be suitable for mounting on the labial and buccal aspects of the arches.

The tooth-moving forces generated by compression of the fluid-filled vesica in the present invention represent a force-generation and force-equalization system that is new to orthodontics. Taking the example of an upper lingual application in FIG. 12, once the orthodontic appliance is placed in the mouth of an orthodontic patient, the labial-most leading edge of the vesica 20 will be compressed by the most lingually-disposed tooth 10 of the group. Any other lingually-disposed teeth 12 presented by the case likewise will deform the vesica 20 whereas any properly positioned teeth may just be lightly touched or "kissed" by the vesica 20. The reader is asked to consider the nature of the violation of the soft and compliant, elastic but taunt, uniformly-curved surface of the vesica by the hard, mal-positioned teeth. The configuration of the rigid tooth will of course not be altered, but the vesica's shape will be locally altered by the errant tooth. At the region of contact between the vesica and the tooth, the vesica will tend to wrap around and comply with the curving surfaces of the lingual tooth anatomy. In doing so, the normal symmetrical shape of the vesica will be violated and the degree of internal pressurization of the vesica liquid will increase slightly. The surface of the vesica in compliance with the lingual anatomy, as well as the material immediately adjacent to the violation interface will be slightly compressed.

Figure 12:
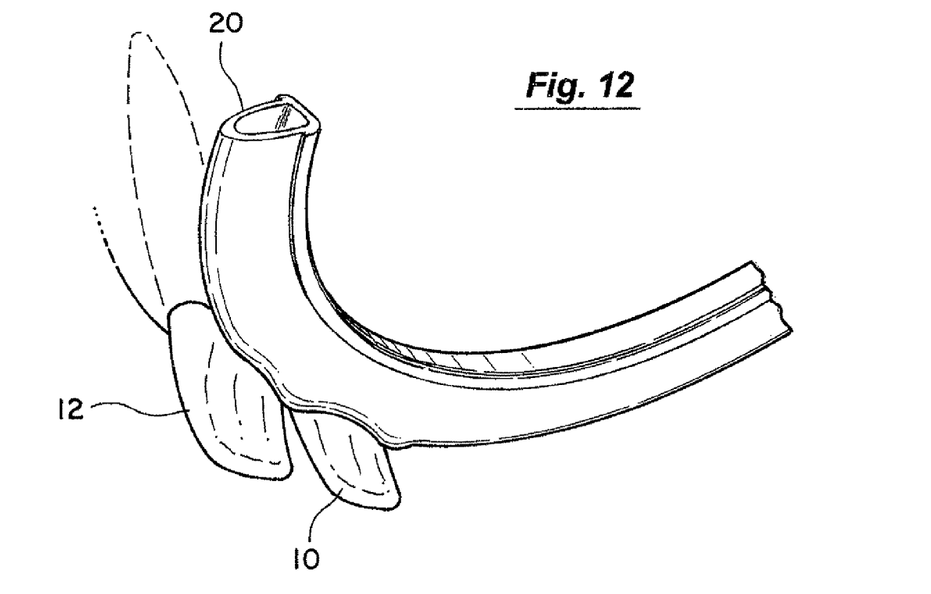
FIG. 12 is a top view illustrating deformation and compression of the vesica 20 by teeth 10, 12.

FIG. 12 is a perspective view of this concept from the lingual aspect of the vesica 20. The vesica 20 is depicted in contact with an upper right central tooth 10 that exhibits a mesial lingual rotation in combination with an undesirable lingual inclination. The accommodation of the generally convex lingual anatomy of the upper central right tooth 10 by the soft, fluid-filled vesica 20 creates a correspondingly concave set of indentation surfaces in the vesica 20. Portions of the vesica 20 immediately adjacent to the concave indentation not only exhibit slightly higher tensile stress as described above but also bulge out as the material attempts to define a minimal surface geometry in compliance with presence of the tooth 10. The degree of bulging and the contour of the bulging areas is a reflection of the resilience, or elastic modulus, bending modulus and wall thickness of the vesica material, and the degree of slight hydraulic pressurization of the liquid 24 contained in the vesica 20. The periphery of the generally concave indentation created by any tooth 10, 12 as it violates and distorts the otherwise passive profile of the vesica 20 can be seen in FIG. 12.

Applying the principles conventionally used in orthodontics for determining the plan-form area of a tooth's root and then determining optimal physiological tooth-moving forces based on an optimal unit force, the same approach can be used to analyze the area of contact between the tooth and the vesica. This is done to determine the magnitude of the forces transferred from the vesica to an errant tooth. A plan-form area of the generally concave indentation of the vesica can be similarly determined and converted to a 2-D plan-form area just as is conventionally done for a tooth's root area. In the example shown in FIG. 12, where the vesica 20 is shown being violated by a maxillary central right tooth 10, we can assume as an example that the plan-form area of violation of the vesica is 24 mm$^2$ and the same unit force of 5 grams per mm$^2$ is used. We can then say that at the degree of violation of the vesica 20 by the tooth 10, the vesica is responding with 5 g/mm$^2$×24 mm$^2$ or 120 g of labially-directed force.

Further, the relationship of the vesica to the tooth can be reevaluated over the course of treatment as the tooth is repositioned and the area of contact between the vesica by the tooth is reduced. A force vector to be exerted by the vesica 20 on a specific tooth and its underlying bone structure can be determined by applying Newton's third law of motion (i.e., to every action there is an equal and opposite reaction) and appropriately combining it with Wolff's law (i.e., altered structure alters function and altered function alters structure). It is feasible to remodel the supporting alveolar bone in such a way as to move the tooth with its socket and supporting bone as a physiologic unit. However, it should be understood that the physiological aspect should taken into account along with the mechanical. When evaluated from the point of view of a living resistant forcer instead of basic Newtonian mechanics, a more comprehensive and complex pictures evolves. Every change in the form or function of a bone is followed by a change in its internal architecture and secondary alternatives in its external conformation (i.e., altered function alters structure and vice versa). Thus, the forces required in a living environment are nonlinear and not constant in nature. In contrast, the same forces acting in a nonliving medium typically result in a constant or linear resistance.

The present invention provides a force-application system that delivers an equal pressure over the entire exterior surface of the vesica, but is inherently differential in the force applied to small teeth versus larger teeth due to the differences in surface contact area. The physical properties of the vesica and the degree of compression of the vesica by the teeth can be selected by the orthodontist to exert a relatively optimal pressure on selected teeth and their associated bone structure using bio-analytical mechanics. The area of hydraulics as an orthodontic active force system affords this unique potential.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. An orthodontic appliance for positioning a patient's teeth comprising:
    a flexible vesica containing a fluid;
    a support structure for attachment to anchor molars and holding the vesica relative to the anchor molars in compression against selected anterior teeth, whereby the fluid within the vesica exerts a therapeutic labially-directed pressure on the selected anterior teeth to move the selected anterior teeth to desired positions relative to the anchor molars;
    a bow for stopping further movement of the selected anterior teeth in response to pressure exerted by the fluid within the vesica beyond the desired positions; and an activation ribbon for insertion between the vesica and support structure, said activation ribbon having a thin elongated shape with a width selected to advance the vesica against the selected anterior teeth.

2. The orthodontic appliance of claim 1 wherein the support structure comprises an arch-shaped trough supporting the vesica.

3. The orthodontic appliance of claim 2 further comprising an activation screw extending through the trough for adjusting the position of the vesica.

4. The orthodontic appliance of claim 1 wherein the vesica is substantially tubular.

5. The orthodontic appliance of claim 1 wherein the fluid is substantially incompressible.

6. The orthodontic appliance of claim 1 wherein the fluid comprises water.

7. The orthodontic appliance of claim 1 wherein the fluid comprises glycerin.

8. The orthodontic appliance of claim 1 further comprising a plurality of activation ribbons of progressively increasing widths for insertion in sequence between the vesica and support structure.

9. An orthodontic appliance for positioning a patient's teeth comprising:
    a flexible, tubular vesica containing a fluid;
    a support structure for attachment to anchor molars holding the vesica relative to the anchor molars in compression against selected anterior teeth, whereby the fluid within the vesica exerts a therapeutic labially-directed pressure on the selected anterior teeth to move the selected anterior teeth to desired positions relative to the anchor molars;
activation means for adjusting the position of the vesica relative to the support structure and anchor molars;
a bow for stopping further movement of the selected anterior teeth in response to pressure exerted by the fluid within the vesica beyond the desired positions; and an activation ribbon for insertion between the vesica and support structure, said activation ribbon having a thin elongated shape with a width selected to advance the vesica.

10. The orthodontic appliance of claim 9 wherein the support structure further comprises an archwire supporting an arch-shaped trough holding the vesica.

11. The orthodontic appliance of claim 10 further comprising an activation screw extending through the trough for adjusting the position of the vesica.

12. The orthodontic appliance of claim 10 wherein the trough of the support structure further comprises at least one barb for engaging a corresponding slot in the vesica.

\* \* \* \* \*